United States Patent [19]
Rockhill

[11] Patent Number: 5,172,147
[45] Date of Patent: Dec. 15, 1992

[54] ROBOTIC PHOTOGRAPHIC APPARATUS FOR HANDICAPPED PERSONS

[76] Inventor: William M. Rockhill, 69 Amherst St., Cumberland, R.I. 02864

[21] Appl. No.: 671,193

[22] Filed: Mar. 18, 1991

[51] Int. Cl.⁵ .............................................. G03B 29/00
[52] U.S. Cl. .................................................. 354/81
[58] Field of Search ...................... 358/93; 354/81, 82, 354/293

[56] References Cited

U.S. PATENT DOCUMENTS 4,420,238  12/1983  Felix ...................................... 354/81
5,012,335  4/1991   Cohodar ................................ 354/81

Primary Examiner—Michael L. Gellner
Assistant Examiner—David M. Gray
Attorney, Agent, or Firm—Salter, Michaelson & Benson

[57] ABSTRACT

A robotic photographic apparatus includes a mounting assembly, first and second arm assemblies, a tilt arm assembly, a track assembly, a carriage assembly, and a controller. The mounting assembly is operative for mounting the apparatus on a wheelchair, and the first and second arm assemblies, the tilt arm assembly, the track assembly, and the carriage assembly are operable by a handicapped person through the controller for positioning, adjusting and operating a camera mounted on the carriage assembly for taking photographs.

15 Claims, 9 Drawing Sheets

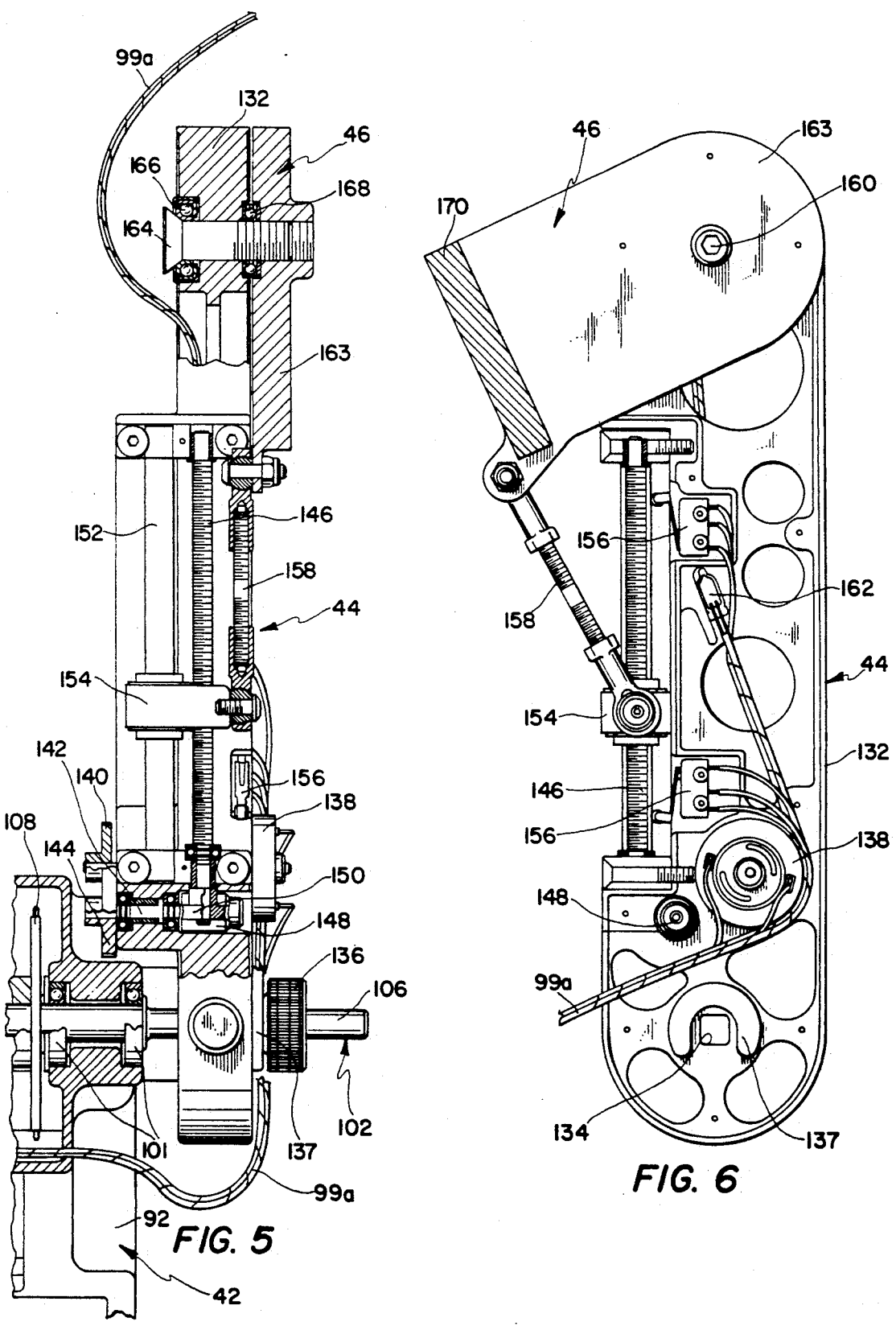

ROBOTIC PHOTOGRAPHIC APPARATUS FOR HANDICAPPED PERSONS

BACKGROUND AND SUMMARY OF THE INVENTION

The instant invention relates to apparatus for assisting physically handicapped persons, and more particularly to a robotic photographic apparatus which is operative by a severely handicapped person for taking photographs.

It has been found that persons suffering from serious physical disabilities frequently also suffer from severe depression. In this connection, it has been found that depression among severely handicapped persons is often caused by a severe lack of self-esteem resulting from an inability to perform many normal activities and functions without assistance. For example, it has been found that patients suffering from irreversible spinal cord injuries, or patients suffering from advanced multiple sclerosis or muscular dystrophy often suffer from severe depression resulting from their inability to perform many daily activities without assistance. Further, it has been found that this is particularly true with respect to quadriplegic patients who are generally confined to wheelchairs and are incapable of performing virtually any normal activities without assistance.

In recent years motorized wheelchairs have been developed which have enabled severely handicapped patients to move about without assistance through the use of various patient operated control systems. Control systems of this type generally interfaced with patients through various patient operated switching devices, such as "sip-and-puff"switches, chin switches, or joy sticks. However, while many handicapped persons have gained at least some mobility through the use of these relatively sophisticated wheelchairs, they have nevertheless generally been unable to perform most other types of activities.

The instant invention represents a significant advancement in the art relating to apparatus for severely handicapped persons by providing a device for enabling a handicapped person, such as a quadriplegic, to take photographs without assistance. More specifically, the instant invention provides a robotic photographic apparatus which is operable by a patient suffering from a severe physical disability for taking photographs at will without assistance other than during initial set-up of the apparatus. Still more specifically, the instant invention provides a robotic photographic apparatus which is operable by a handicapped patient having a severe upper body disability for robotically operating a camera while the patient is seated in a chair, such as a wheelchair. The apparatus of the instant invention comprises manipulating means for robotically holding and manipulating a camera, mounting means for mounting the manipulating means on the chair, and control means operable by the patient for controlling the operation of the manipulating means while seated in the chair. The manipulating means is operable through the control means for moving the camera between an operative position wherein the camera is positioned in front of the face of the patient and an inoperative position wherein the camera is removed from in front of the face of the patient. The manipulating means preferably includes first and second arm portions, and the second arm portion is preferably pivotable relative to the first arm portion for raising and lowering the camera between the inoperative and operative positions thereof. The mounting means is preferably operable for mounting the first arm portion so that it is adjustably positionable relative to the chair, but so that the first arm portion is normally substantially stationary during operation of the manipulating means with the control means. The manipulating means preferably further includes means for rotating the camera about the axis of the viewfinder thereof, and means for tilting the camera in order to tilt the axis of the viewfinder thereof upwardly or downwardly. The apparatus is preferably operable with a camera having an adjustable zoom lens and the manipulating means preferably further includes means for adjusting the zoom lens of the camera. The apparatus is preferably adapted for use in connection with a camera having an automatically adjustable focus, and the manipulating means preferably includes means for actuating the automatic focus of the camera. Still further, the apparatus is preferably operable with a camera having a flash accessory, and the manipulating means preferably includes means for manipulating the camera to enable the flash so that it is actuated with the shutter of the camera. The means for rotating the camera about the axis of the viewfinder preferably includes an arcuate track member on the second arm portion of the manipulating means and a carriage member on the track member. Further, the camera is preferably mounted on the carriage member and the carriage member is preferably movable along the track member for rotating the camera about the axis of the viewfinder thereof.

The photographic apparatus of the instant invention is preferably adapted for adjustably positioning a camera in an operative position which is related to a predetermined orientation and position of the patient's head. Specifically, the apparatus is adapted for positioning the viewfinder of the camera in front of an eye of the patient when the patient's head is in the predetermined orientation and position thereof so that the camera can be rotated and/or tilted relative to the eye for locating and positioning the photographic subject in the viewfinder. The apparatus is preferably utilized in combination with a wheelchair which is controllable by the patient for laterally adjusting the position of a photographic subject relative to the viewfinder. Further, the tilt means is preferably adapted so that it is operative for tilting the camera about a pivot point which is located at approximately the geometric center of one of the patient's eyeballs, but which in any case is spaced from the lens of the viewfinder of the camera by between ¼" and 3". Still further, the manipulating means is preferably operative for positioning the camera at an angle of approximately 20° to a forwardly facing direction of the patient in order to provide clearance for the nose of the patient when the camera is moved to an operative position.

It has been found that the apparatus of the instant invention can be effectively utilized by a severely handicapped patient, such as a quadriplegic patient, for enabling the patient to take photographs. Specifically, it has been found that the apparatus of the instant invention can be effectively utilized by a patient for manipulating and orienting a camera so that the patient can even exhibit a certain degree of artistic ability in taking photographs without the aid of other persons. Specifically, it has been found that the manipulating means of the apparatus can be effectively operated for positioning a camera in a normal photographing position relative to the patient. It has been further found that the manipulating means can be effectively operated for rotating the camera to adjust the position thereof relative to a photographic subject. Still further, it has been found that because the apparatus is adapted for tilting a camera about a point which is preferably located at approximately the geometric center of the eyeball of the patient, the camera can be effectively tilted to further adjust the position thereof relative to a photographic subject without causing the patient to lose his or her vision through the viewfinder.

Accordingly, it is a primary object of the instant invention to provide an effective apparatus for enabling a severely handicapped patient to take photographs.

Another object of the instant invention is to provide an apparatus for enabling a severely handicapped patient to effectively manipulate a camera to take photographs of various photographic subjects.

An even further object of the instant invention is to provide an effective apparatus which is securable to a wheelchair and operative for positioning a camera so that an occupant of the wheelchair can take photographs.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 5 is a front elevational view of the second arm portion and the tilt arm;

FIG. 6 is a side elevational view of the second arm portion and the tilt arm;

DESCRIPTION OF THE INVENTION

Figure 1:
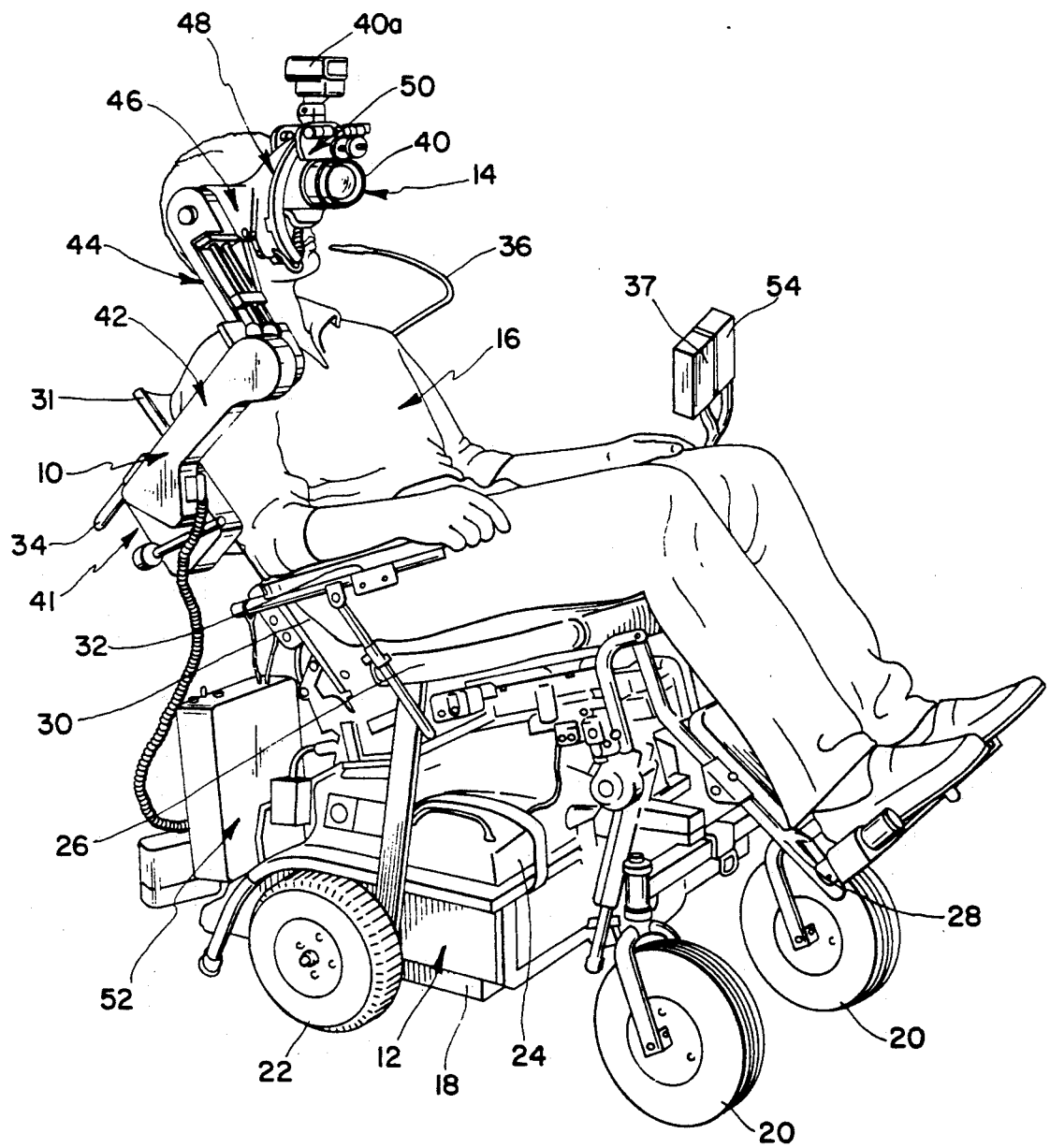
FIG. 1 is a perspective view of the apparatus of the instant invention as operated by a quadriplegic patient in a wheelchair.
Figure 2:
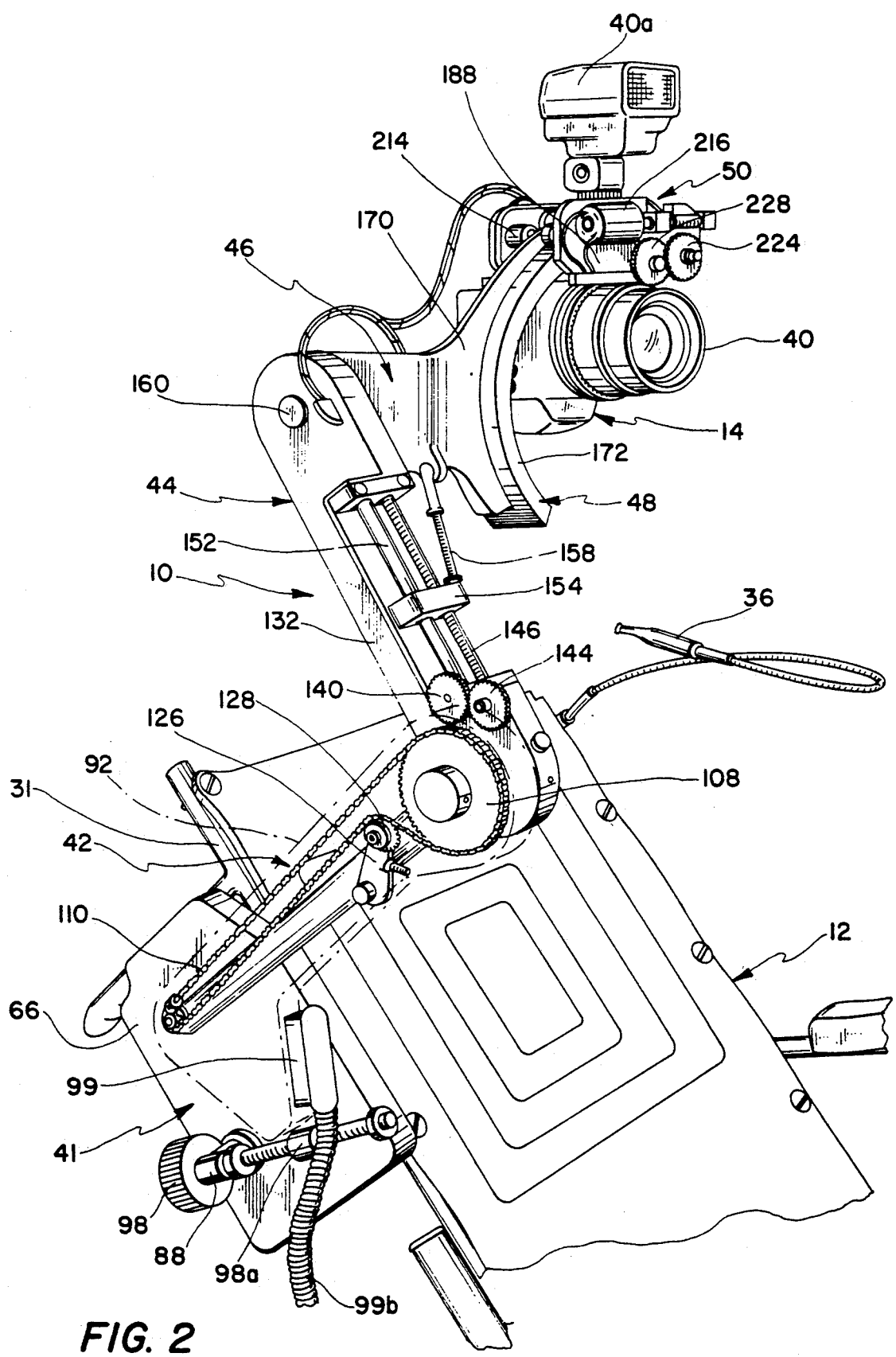
FIG. 2 is an enlarged perspective view of the apparatus mounted on a wheelchair.

Referring now to the drawings, the apparatus of the instant invention is illustrated in FIGS. 1 through 11, and generally indicated at 10 in FIGS. 1 and 2. The apparatus 10 is adapted to be mounted on a wheelchair generally indicated at 12 for supporting a camera generally indicated at 14 thereon, so that the camera 14 can be robotically operated by a severely handicapped patient or operator 16 seated in the wheelchair 12. In this connection, the apparatus 10 is adapted so that it is operable for moving the camera 14 between the operative position illustrated in FIG. 1 wherein the camera 14 is located in front of the face of the patient 16, and an inoperative position wherein the camera 14 is removed from in front of the face of the operator 16. The apparatus 10 is further operative by the operator 16 for adjusting the orientation of the camera 14 relative to a photographic subject, and for adjusting various features of the camera 14, such as zoom lens and flash features.

The wheelchair 12 is of conventional construction and as herein embodied the wheelchair 12 comprises a conventional motorized wheelchair manufactured by Fortress Scientific Company. The wheelchair 12 includes a chassis 18 having front and rear wheel assemblies 20 and 22, respectively, mounted thereon, a battery-powered drive assembly 24, and a seat assembly 26, including a footrest portion 28 and a backrest portion 30 having a frame 31. The wheelchair 12 further includes a pair of armrests 32 and a pair of handles 34 which extend rearwardly from the backrest portion 30 to enable the wheelchair 12 to be more easily manipulated by an attendant. The wheelchair 12 also includes a controller (not shown) of conventional construction which is operative for controlling the operation of the wheelchair 12, a sip-and-puff control member 36, and an annunciator 37. In this regard, the control member 36 is connected to the controller of the wheelchair 12 so that the patient 16 can control the operation of the wheelchair 12 by sipping and/or puffing on the control member 36, and the annunciator 37 is connected to the controller of the wheelchair 12 for displaying information relating to the operation of the controller to the patient 16. The annunciator 37 is mounted on one of the armrests 32 so that it is positioned in front of the patient 16 to enable the patient 16 to observe the annunciator 37 in order to more effectively and easily control the operation of the wheelchair 12. The wheelchair 12 is specifically selected so that the controller thereof is operative in an environmental control or accessory mode and so that it can be readily interfaced with an auxiliary apparatus for controlling the operation of the auxiliary apparatus through a pair of environmental control or accessory relays of the controller. Accordingly, the apparatus 10 can be effectively interfaced with the controller of the wheelchair 12 so that the apparatus 10 can be effectively controlled by manipulating the control member 36. It will be understood, however, that the wheelchair 12 could alternatively be embodied with various other conventional control units which are adapted to be controlled through various other types of control members, including chin switches, tongue switches, etc. It will be further understood that as another alternative the apparatus 10 could be adapted so that it is controllable independently of the wheelchair 12.

The camera 14 is of conventional construction and it preferably comprises a conventional automatic camera including a viewfinder 38 having a viewfinder axis 39, a zoom lens assembly 40, and a flash attachment 40a. As herein embodied, the camera 14 comprises a Nikon camera body model no. N8008 equipped with an AF Nikkor 28–85 mm F1:3.5–4.5 autofocus lens. The camera 14 as herein embodied includes an autofocus function which is actuated with a shutter release button, a motorized film advance, a "rotate to zoom" type lens, and a remote shutter control input.

The apparatus 10 comprises a mounting base assembly generally indicated at 41, a first arm assembly generally indicated at 42, a second arm assembly generally indicated at 44, a tilt arm assembly generally indicated at 46, a track assembly 48, and a carriage assembly 50.

The apparatus 10 further includes a controller 52 which is interfaced with the controller (not shown) of the wheelchair 12 so that the apparatus 10 can be operated by manipulating the control member 36. The controller 52 includes an annunciator 54 and it is adapted so that it can be operated by manipulating the control member 36 for moving the apparatus 10 between the operative and inoperative positions thereof, and so that it can be further operated for tilting the camera 14 and for rotating the camera 14 about the axis 39 of the viewfinder 38 thereof. The controller 52 is further adapted so that the control member 36 can be manipulated for controlling various other operational functions associated with the camera 14, and for operating the shutter of the camera 14 to take photographs.

Figure 3:
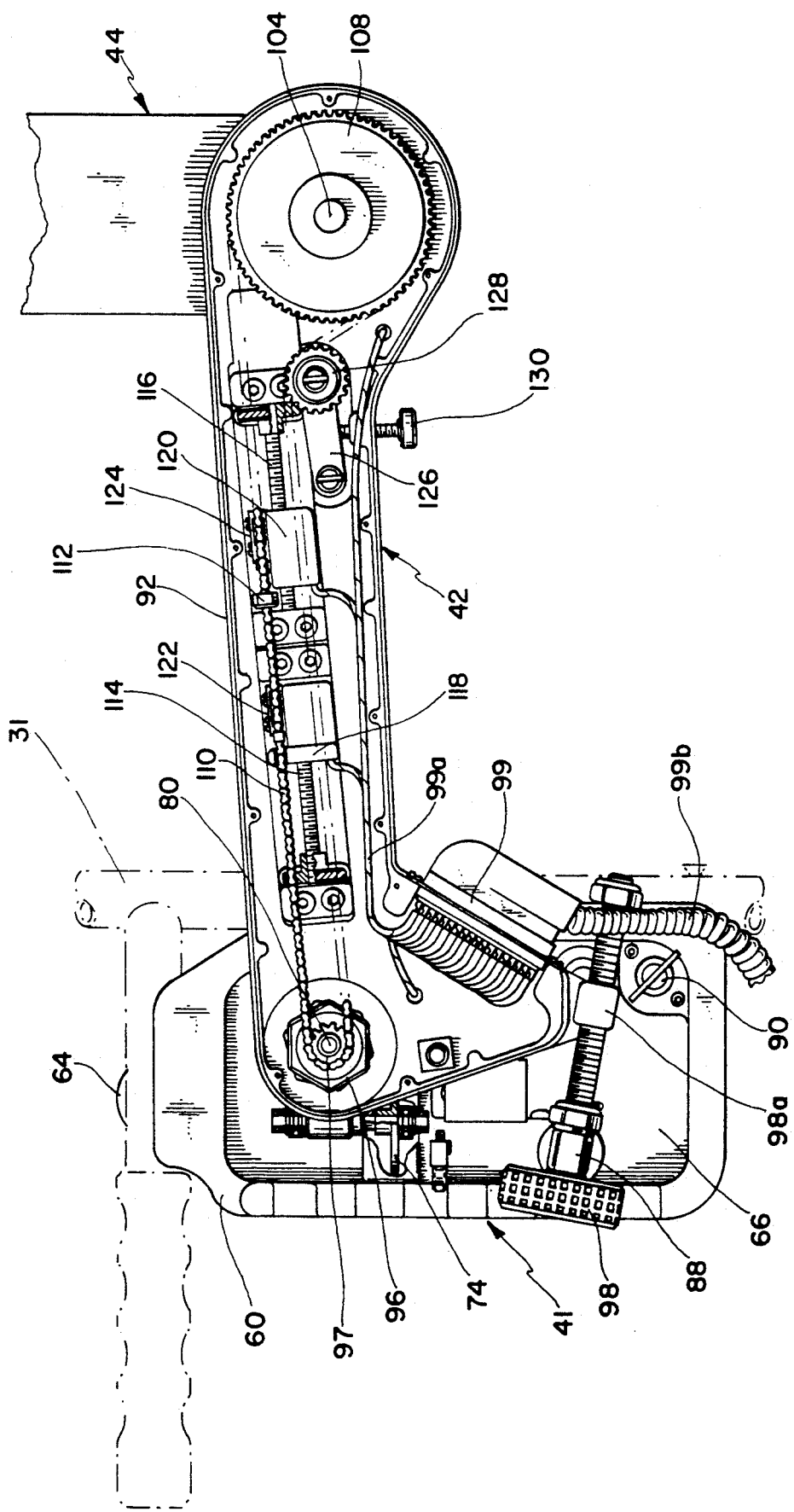
FIG. 3 is a side elevational view of the mounting assembly and the first arm portion of the apparatus.
Figure 4:
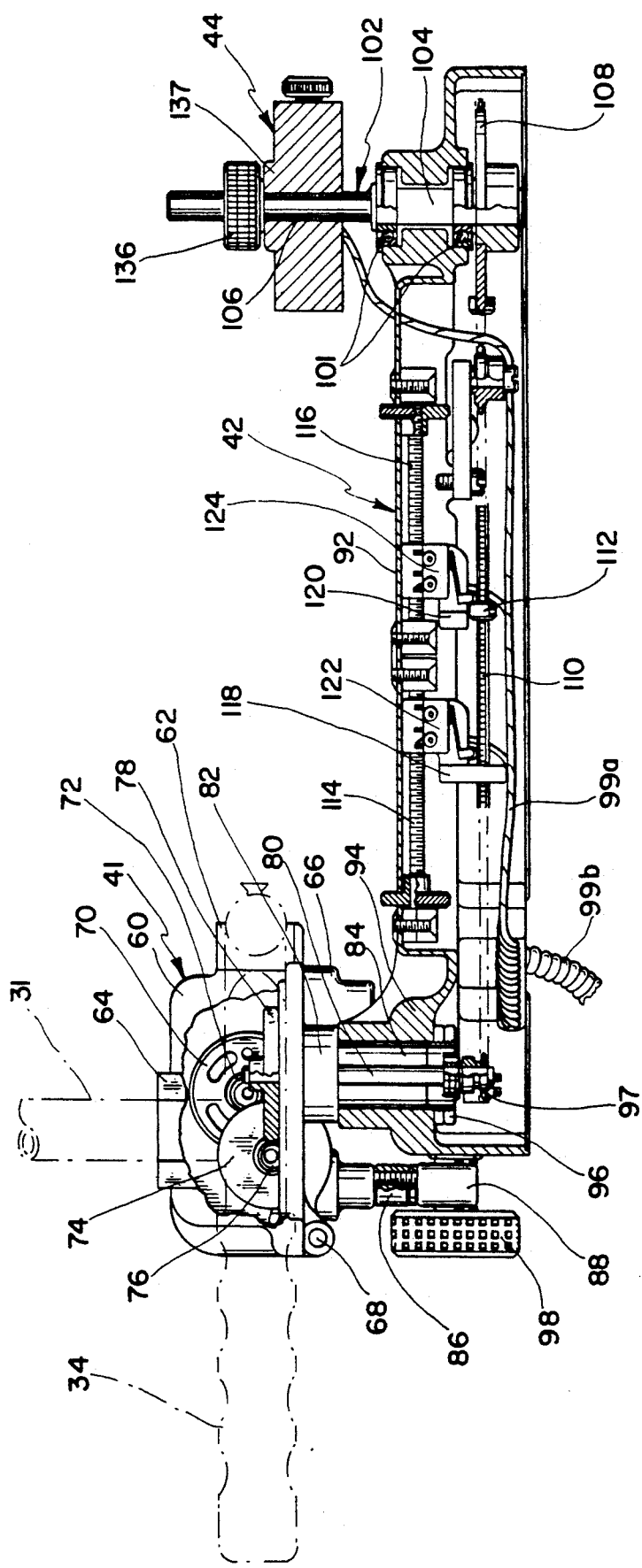
FIG. 4 is a top plan view of the mounting assembly and the first arm portion.
Figure 7:
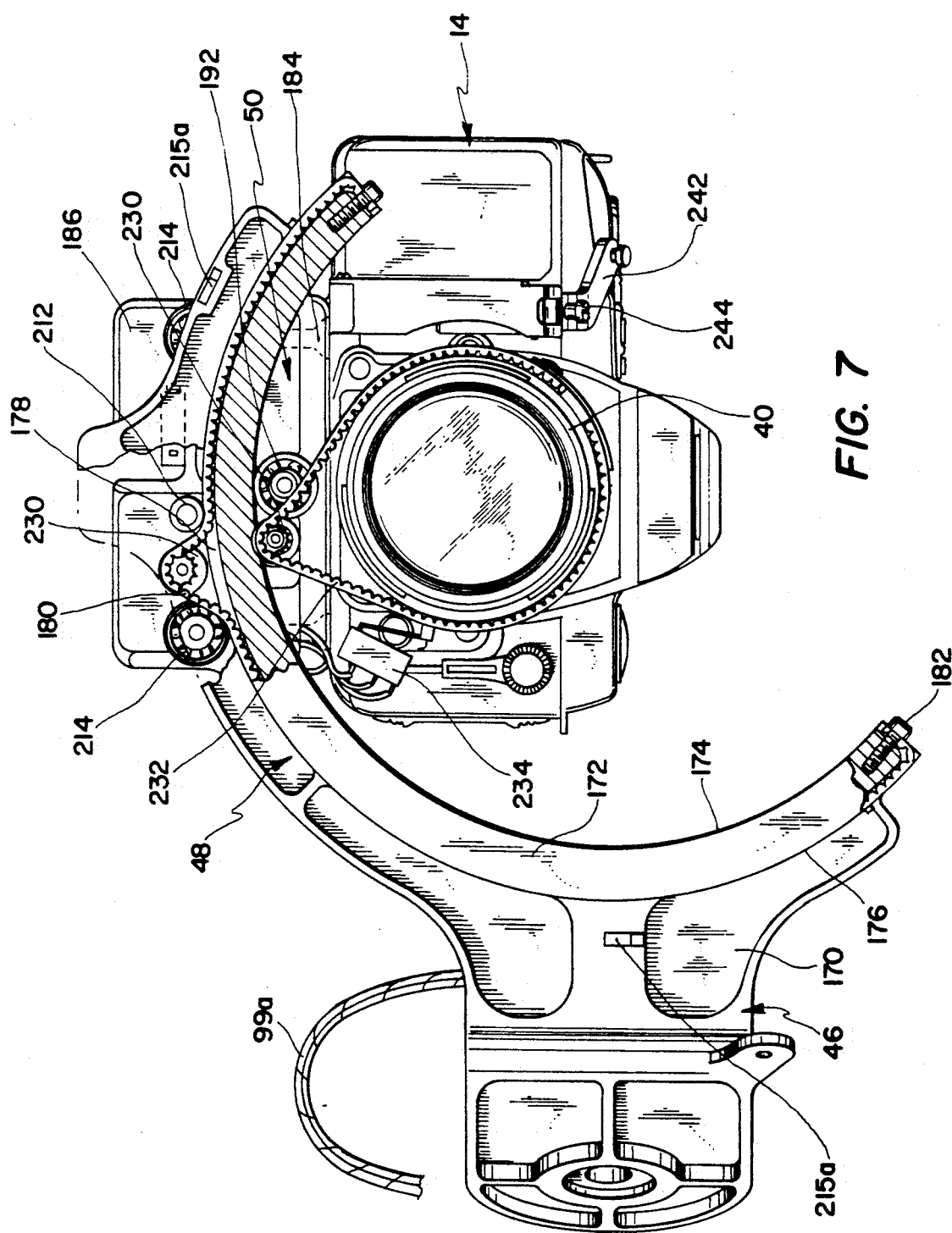
FIG. 7 is a front elevational view of the camera mounting assembly with a camera mounted thereon.
Figure 8:
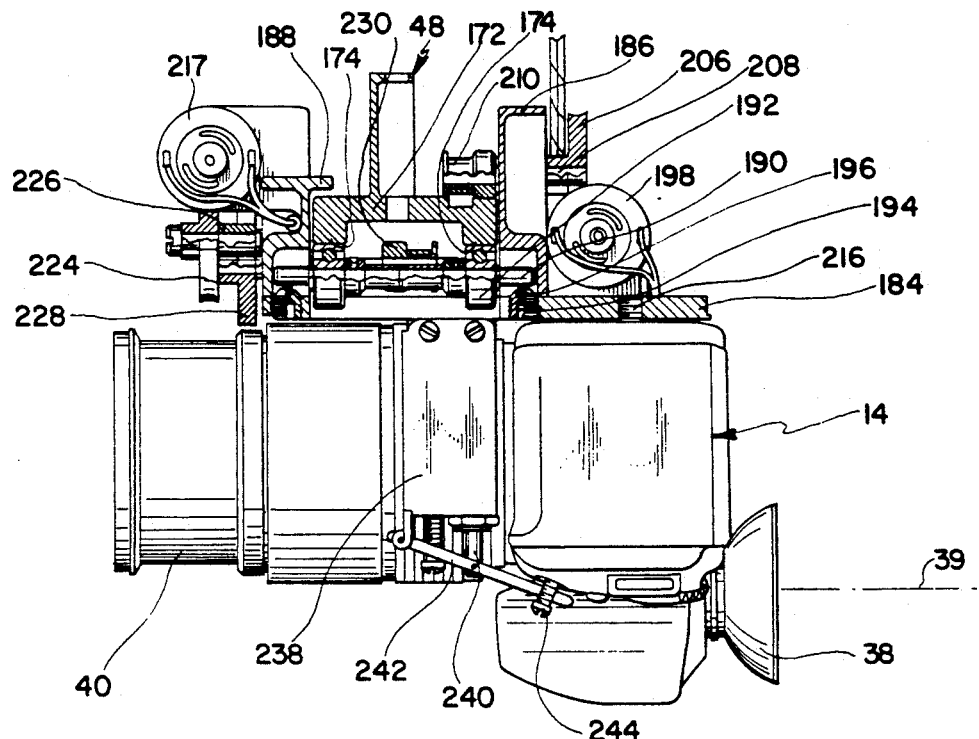
FIG. 8 is a side elevational view of the camera mounting assembly with a camera mounted thereon.
Figure 9:
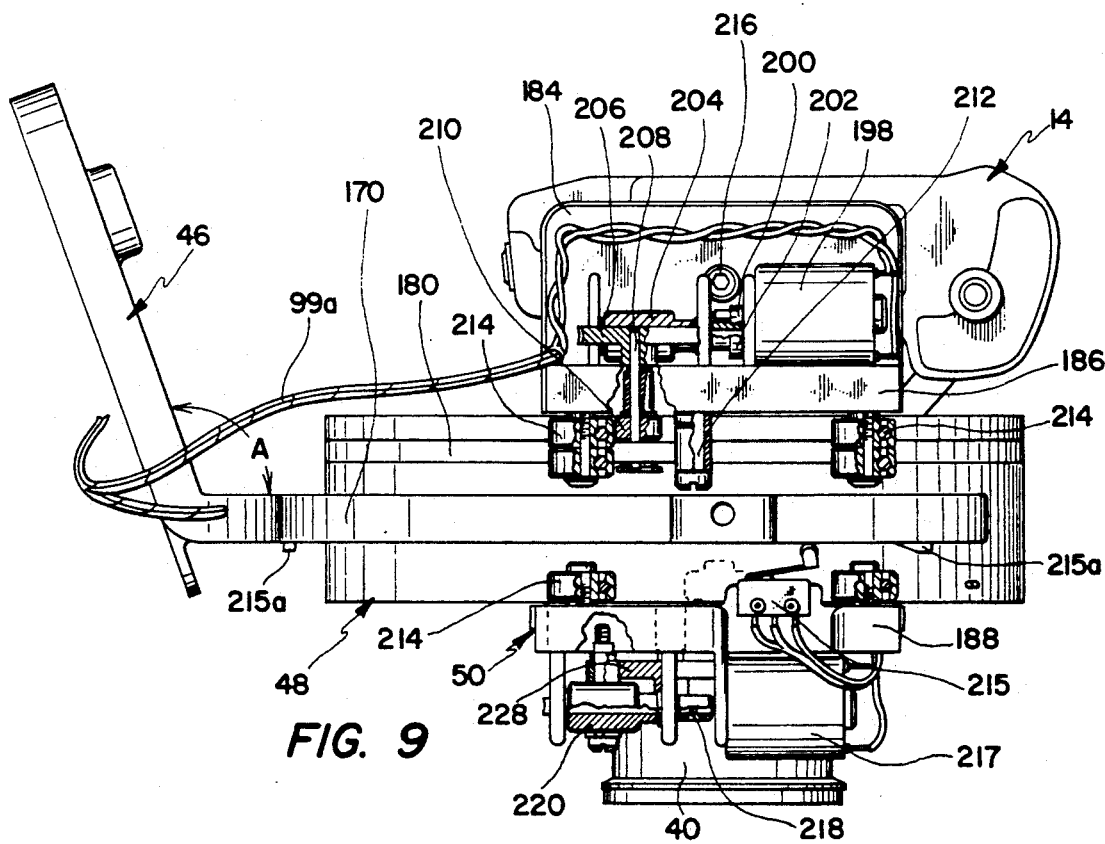
FIG. 9 is a top plan view of the camera mounting assembly with a camera mounted thereon.

The mounting base assembly 41 is illustrated most clearly in FIGS. 2 through 4. The mounting base assembly 41 as herein embodied is specifically adapted to interfit with a Fortress Scientific electric wheelchair. It will be understood, however, that the mounting base assembly 41 can alternatively be adapted for use in connection with a variety of other different types of wheelchairs. In any event, the important point is that the mounting base assembly 41 is adapted to be rigidly secured to the wheelchair 12 so that it can be effectively utilized for supporting the remainder of the apparatus 10 as the apparatus 10 is operated for taking photographs with the camera 14. The mounting base assembly 41 comprises a housing 60 which includes an interfitting recessed mounting bracket portion 62 and a yoke-type bracket 64. The bracket 62 is adapted to be received in interfitting relation with one of the vertical members of the backrest frame 31 and secured thereto with one or more screws, and the yoke bracket 64 is adapted to be received over a horizontally extending section of the frame 31 so that the brackets 64 and 62 cooperate to rigidly secure the housing 60 to the frame 31. The mounting base assembly 41 further comprises a door assembly 66 which is pivotally attached to the housing 60 along a pivot axis 68 so that the door assembly 66 is hingeable outwardly with respect to the housing 60, but so that the door 66 is nevertheless detachable from the housing 60. Mounted on the inner side of the door 66 is a motor 70 having a pinion gear 72 thereon which communicates with a spur gear 74 and a worm gear 76 which is co-axially mounted with the spur gear 74 so that it intermeshes with a worm wheel 78. The worm wheel 78 is mounted on drive shaft 80 which passes through a hub 82 and then through a neck 84, both of which are integrally formed with the door 66. As herein embodied, the motor 70 comprises a 6990 RPM 12 volt DC motor and the gears 72, 74, 76 and 78 cooperate to provide a 160:1 gear reduction, although obviously the apparatus 10 can alternatively be embodied with a variety of different motors and gear reductions in the mounting base assembly 41. Also included in the mounting base assembly 41 is a mount 86 which extends outwardly from the door 66 terminating in a collar or pivot block 88. Suitable means, such as a DZEUS (TM) fastening assembly 90, is provided for releasably retaining the door 66 in the closed position thereof with respect to the housing 60 as illustrated in FIGS. 1 through 4. As will be seen from FIG. 4, when the door 66 is in the closed position thereof, the motor 70 and the gears 72, 74, 76 and 78 are located in the interior of the housing 60 so that the shaft 80 extends outwardly toward the side of the wheelchair 12.

The first arm assembly 42 comprises an elongated housing 92 having a tubular sleeve portion 94 formed at one end thereof. The sleeve portion 94 is received on the neck 84 so that the shaft 80 passes through the sleeve portion 94, and a pair of nuts 96 are threadedly received on the neck 84 for rotatably retaining the first arm assembly 42 on the mounting base assembly 41. The shaft 80 extends through the neck 84, and a sprocket 97 is received thereon so that the sprocket 97 is positioned within the housing 92 and rotates with the shaft 80 when the motor 70 is energized. An adjustment screw 98 is rotatably mounted in the pivot block 88 and threadedly received in a height adjustment drive block 98a for adjusting the angle of the first arm assembly 42. A multipin electrical terminal assembly 99 is provided in the first arm assembly for connecting an internal wiring harness 99a to an external wiring harness 99b which extends to the controller 52. Located at the opposite end of the housing 92 from the sleeve portion 94 is a pair of bearings 101 which are operative for rotatably mounting a shaft generally indicated at 102. The shaft 102 includes a cylindrical portion 104 which is rotatably received in the bearings 101 and a drive portion 106 of substantially square cross-section which is threaded at the corners thereof. Mounted on the cylindrical portion 104 of the shaft 102 is a sprocket 108, and a drive chain 110 extends between the sprockets 97 and 108 for rotating the shaft 102. A chain collar 112 is provided on the chain 110, and up and down limit shafts 114 and 116, respectively, are rotatably mounted in the housing 92 in substantially parallel, spaced relation to the chain 110. Mounted on the shafts 114 and 116 are up and down limit blocks 118 and 120, respectively, having up and down limit switches 122 and 124, respectively, mounted thereon. The limit blocks 118 and 120 are adjustably positionable in the housing 92 for adjusting the positions of the limit switches 122 and 124. The limit switches 122 and 124 are positioned for engaging the chain collar 112 in order to limit the extent to which the chain 110 is movable in the housing 92, and the limit block 118 mechanically prevents movement of the chain 110 beyond a predetermined limit position. Also provided in the first arm assembly 42 is a pivotally mounted tension arm 126 having a tension gear 128 thereon. The tension gear 128 is mounted so that it engages the chain 110, and a tensioning screw 130 engages the arm 126 to adjust the tension applied to the chain 110 by the gear 128.

The second arm assembly 44 is illustrated most clearly in FIGS. 4 through 6, and it includes an elongated housing or frame 132. Formed at one end of the frame 132 is a substantially square aperture 134 in which the drive portion 106 of the shaft 102 is received, and a nut 136 which is interlocked in a retaining collar 137 on the frame 132 of the second arm assembly 44 is threadedly received on the shaft 106 to retain the second arm assembly 44 thereon so that it pivots with the shaft 102. Further, because the nut 136 is interlocked in the retaining collar 137, the nut 136 is actually operative for defining the lateral position of the second arm assembly 44 on the shaft 102 so that the nut 136 can be utilized for adjusting the lateral position of the second arm assembly 44. Contained within the second arm assembly 44 is a second arm drive motor 138 having a second arm drive gear 140 mounted thereon. Rotatably mounted on a shaft 142 in the second arm assembly 44 is a spur gear 144 which intermeshes with the second arm drive gear 140 for rotating the shaft 142 when the motor 138 is energized. An elongated threaded shaft 146 is rotatably mounted in the second arm assembly 44 in a substantially longitudinally extending orientation, and a worm gear 148 on the shaft 142 intermeshes with a worm wheel 150 on the shaft 146 for rotating the shaft 146 when the motor 138 is energized. In this connection in the embodiment herein set forth, the second arm drive motor 138 comprises a 3680 RPM DC motor and the gears 140, 144, 148 and 150 cooperate to provide a gear reduction of approximately 20:1 so that the threaded shaft 146 is normally rotated at a rate of approximately 180 RPMs when the motor 138 is energized. It will be understood, however, that a variety of other embodiments which include different types of gear arrangements, etc., in the second arm assembly 44 are contemplated. The second arm assembly 44 further includes an elongated guide shaft 152 which is mounted in substantially parallel relation to the threaded shaft 146, and a drive member 154 which is slidably received on the guide shaft 152 and received in threaded engagement on the threaded shaft 146 so that it travels along the length of the shaft 146 as the shaft 146 is rotated. A pair of limit switches 156 are mounted in spaced relation on the frame 132 adjacent the shaft 146 so that they are engageable by the drive member 154 for limiting the travel of the slide member 154 on the threaded shaft 146. A connecting rod 158 of adjustable length extends from the drive member 154 to the tilt arm 46 for tilting the tilt arm 46 about an axis 160. A pair of mercury switches 162 (only one shown) are provided for deactivating the prefocus and shutter functions of the camera 14 when the second arm assembly 44 and the camera 14 are in inoperative positions.

The tilt arm assembly 46 includes a face plate portion 163, and it is pivotally mounted on the outer end of the second arm assembly 44 with a screw 164 which is received in threaded engagement in the face plate portion 163. The screw 164 is mounted in bearings 166 and 168 on the outer end of the second arm assembly 44 so that the face plate portion 163 is rotatable about the axis 160 for tilting the tilt arm 46. The tilt arm 46 further includes an angular arm portion 170 which extends angularly inwardly in front of the operator 16 at an angle "A" of approximately 110°. Accordingly, since the first and second arm assemblies 42 and 44, respectively, are disposed in substantially parallel relation to the forward line of vision of the operator 16 when the operator 16 is seated in the wheelchair 12, the angular arm portion 170 is located in a plane which is angled outwardly toward the side of the operator 16 at an angle of approximately 20° rather than being positioned directly in front of the operator 16. In other words, instead of being located in directly perpendicular relation to the direct line of vision of the operator 16, the angular portion 170 is angled outwardly at an angle of approximately 20° relative to a forward direction so that it is actually located at an angle of approximately 110° to the direct forward line of sight of the operator 16. This enables the camera 14 to be positioned in a more natural orientation relative to the face of the operator 16 so as to provide clearance for the operator's nose. As illustrated in FIGS. 5 and 6, the connecting rod 158 is pivotally connected to the face plate portion 163 adjacent the angular arm portion 170 for pivoting the pivot arm assembly 46 about the axis 160 as the drive member 154 is repositioned on the threaded shaft 146 by the motor 138.

The track assembly 48 preferably comprises a track frame 172 which is integrally formed in substantially parallel relation with the angular arm portion 170. The track frame 172 is of arcuate configuration and it extends over an arc of approximately 180°. The track frame 172 includes a pair of spaced arcuate inner surfaces 174, and an arcuate outer surface 176 having a channel 178 formed therein. The radial dimension of the track frame 172 is adapted such that as the camera 14 and the carriage assembly 50 travel around the arcuate frame member 172, the camera 14 is rotated about the viewfinder axis 39 thereof as will hereinafter be more fully set forth. Also included in the track assembly 48 is a multi-toothed belt 180 which is received in the channel 178 so that the teeth of the belt 180 face inwardly toward the track frame 172, the belt 180 being secured to opposite ends of the track frame 172 with screws 182.

The carriage assembly 50 includes a camera mounting plate 184 and a roll mounting plate 186 and a zoom mounting plate 188 which are mounted on the camera mounting plate 184. A lower bearing shaft 190 having a pair of ball bearings 192 thereon is secured in the carriage assembly 50 so that opposite ends of the shaft 190 are received in slots in the roll drive plate 186 and the zoom drive plate 188, and set screws 194 in the camera mounting plate 184 compress springs 196 to positions of engagement with opposite end portions of the shaft 190 in order to maintain the bearings 192 in pressurized engagement with the inner surfaces 174 of the track frame member 172. A roll drive motor 198 having an output of 5040 RPMs is mounted on the roll drive plate 186, and a pinion gear 200 is mounted on the shaft of the motor 198. The pinion gear 200 intermeshes with a spur gear 202 for rotating a worm gear 204, and the worm gear 204 intermeshes with a worm wheel 206 for driving a shaft 208 which is rotatably mounted in the roll drive plate 186. The pinion gear 200, the spur gear 202, the worm gear 204 and the worm wheel 206 cooperate to provide a gear reduction of approximately 240:1. Mounted on the shaft 208 in front of the roll drive plate 186 is a multi-toothed roll output pulley 210. The multi-toothed belt 180 extends in intermeshing relation over the periphery of the output pulley 210, and an idler roller 212 is rotatably mounted on the roll drive plate 186 adjacent the output pulley 210 for engaging the outer surface of the belt 180 to maintain it in intermeshing relation with the pulley 210. A pair of upper bearing assemblies 214 are mounted in spaced relation on the roll drive plate 186 for engaging the upper surface 176 of the track frame portion 172. Accordingly, the bearing 214 cooperates with the bearings 192 to mount the carriage assembly 50 on the track frame 172 so that the carriage assembly 50 can be advanced along the track frame 172 with the multi-toothed belt 80 as the motor 198 is energized to rotate the roll drive pulley 210. A microswitch 215 on the plate 188 is engageable with bumps 215a on the track frame 172 for limiting the travel of the carriage assembly 50 thereon.

The camera 14 is attached to the camera mounting plate 184 with a screw 216 so that the camera 14 and the camera mounting plate 184 are positioned on the inner side of the track frame 172. As hereinabove noted, the track assembly 48 and the carriage assembly 50 are specifically dimensioned and configured so that as the camera 14 and the carriage assembly 50 travel along the track frame 172, the camera 14 is pivoted about a center of rotation which is coaxial with the axis 39 of the viewfinder 38. Accordingly, while the rotational position of the viewfinder 38 is changed with respect to an eye of the operator 16 looking through the viewfinder 38, the viewfinder 38 remains in an aligned position in front of the operator's eye so that the head of the operator 16 does not have to be repositioned relative to the viewfinder 38.

The carriage assembly 50 further comprises a zoom motor 217 which is mounted on the zoom drive plate 188, and a coupling shaft 218 extends from the motor 217 to a worm gear 220. The worm gear 220 intermeshes with a worm wheel 224 which drives a spur gear 226 and the spur gear 226 intermeshes with a spur gear 228. Co-axially mounted on a common shaft with the spur gear 228 is a zoom drive pulley 230 which intermeshes with a multi-toothed belt 232. As illustrated most clearly in FIG. 7, the belt 232 extends in gripping engagement around the zoom lens portion 40 of the camera 14 so that the zoom lens portion 40 can be rotated with the belt 232 to adjust the zoom lens 40 of the camera 14 by rotating the zoom drive pulley 230 with the zoom motor 217. A limit switch 234 is attached to the camera mounting plate 184 so that it is engageable by protrusions (not shown) on the zoom lens 40 for limiting the extent of rotation of the zoom lens 40.

Also included in the carriage assembly 50 and mounted on the camera mounting plate 184 is a solenoid mounting bracket 238 and a solenoid 240 which is mounted on the bracket 238. Pivotally attached to both the bracket 238 and the solenoid 240 is a prefocus arm 242 having an adjustment screw 244 thereon. The prefocus arm 242 is operative with the solenoid 240 for partially depressing the shutter release button of the camera 14 in order to actuate the auto-focus function of the camera 14 without actually tripping the shutter thereof. The amount by which the shutter release button of the camera 14 is depressed can be adjusted with the adjustment screw 244 to assure that the shutter of the camera 14 is not inadvertently tripped when the solenoid 240 is actuated.

Figure 10:
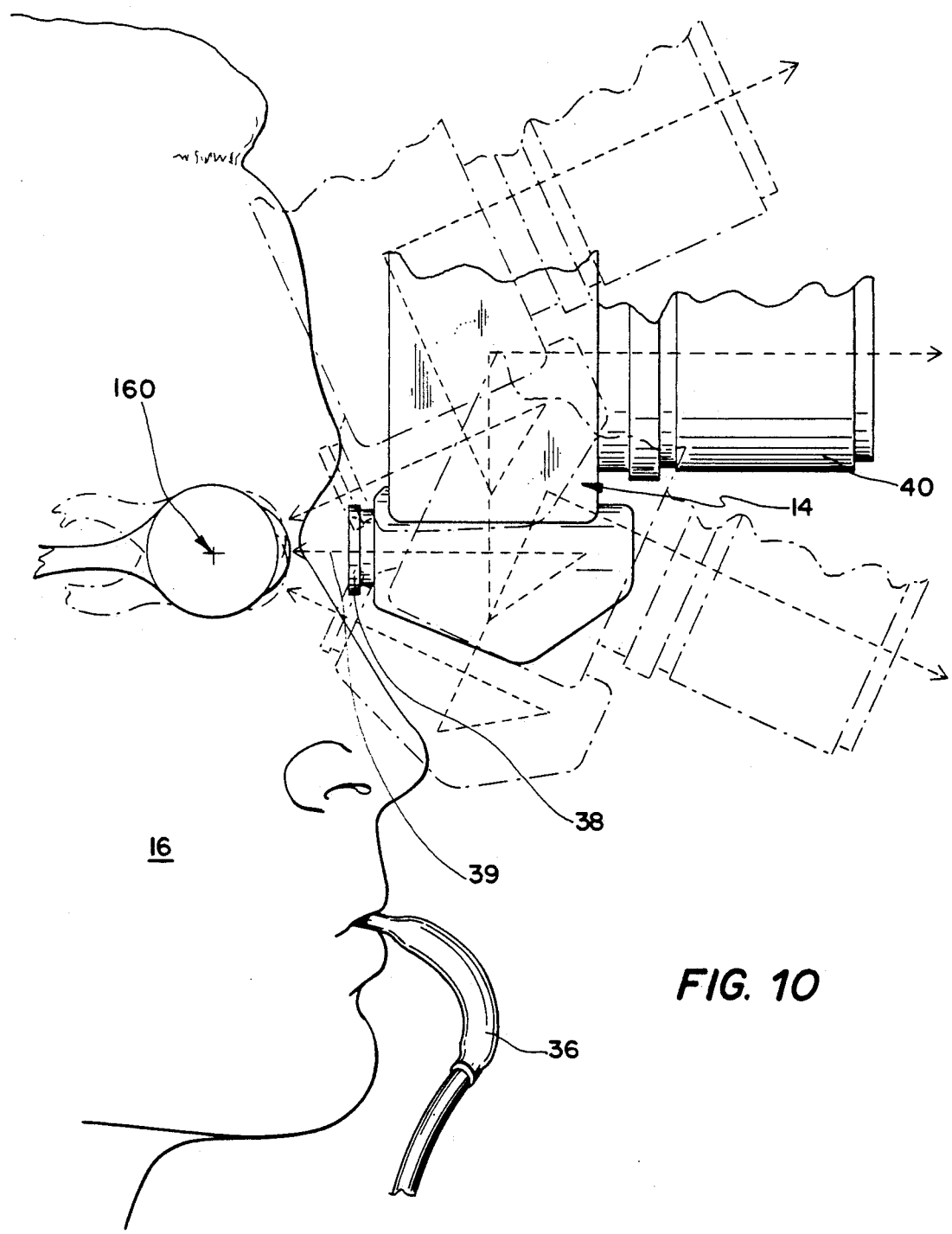
FIG. 10 is a schematic view illustrating the tilting action of the apparatus.

Referring now to FIG. 10, the operation of the tilt feature of the apparatus 10 as carried out utilizing the second arm portion 44 and the tilt arm portion 46 is illustrated. As will be noted, in order for the tilt function to operate effectively it is important for the camera 14 to tilt about an axis which allows the operator 16 to observe a photographic subject through the viewfinder 38 without requiring head movement on the part of the operator 16. It has been determined that this axis of rotation preferably lies along the axis 39 of the viewfinder 38 and that it is located at approximately the center of the eyeball utilized for viewing through the viewfinder 38. However, for practical reasons this may not always be possible since the configuration of a particular camera 14 may cause the camera 14 to engage the operator's forehead if the operator's forehead is located too close to the viewfinder 38. It has been found that although the ideal orientation of the camera 14 relative to the eye of the operator 16 looking through the viewfinder 38 is such that the camera 14 pivots about an axis which is located at approximately the center of the eyeball, it is nevertheless possible to locate the camera 14 so that it pivots about an axis which is between approximately ⅞" and 3" from the lens of the viewfinder 38. Bearing this in mind it will be understood that the pivot arm 46, the track assembly 48, and the carriage assembly 50, are all constructed and dimensioned so that when the pivot arm 46 pivots about the pivot axis 160, the camera 14 is pivoted such that the viewfinder axis 39 pivots about an axis which is spaced from the lens of the viewfinder 38 by a distance which is between ⅞" and 3". Further, because of the geometry of the apparatus 10 it will be apparent that the actual pivot axis of the viewfinder axis 39 is located at the point of intersection between the pivot axis 160 and the viewfinder axis 39.

Figure 11:
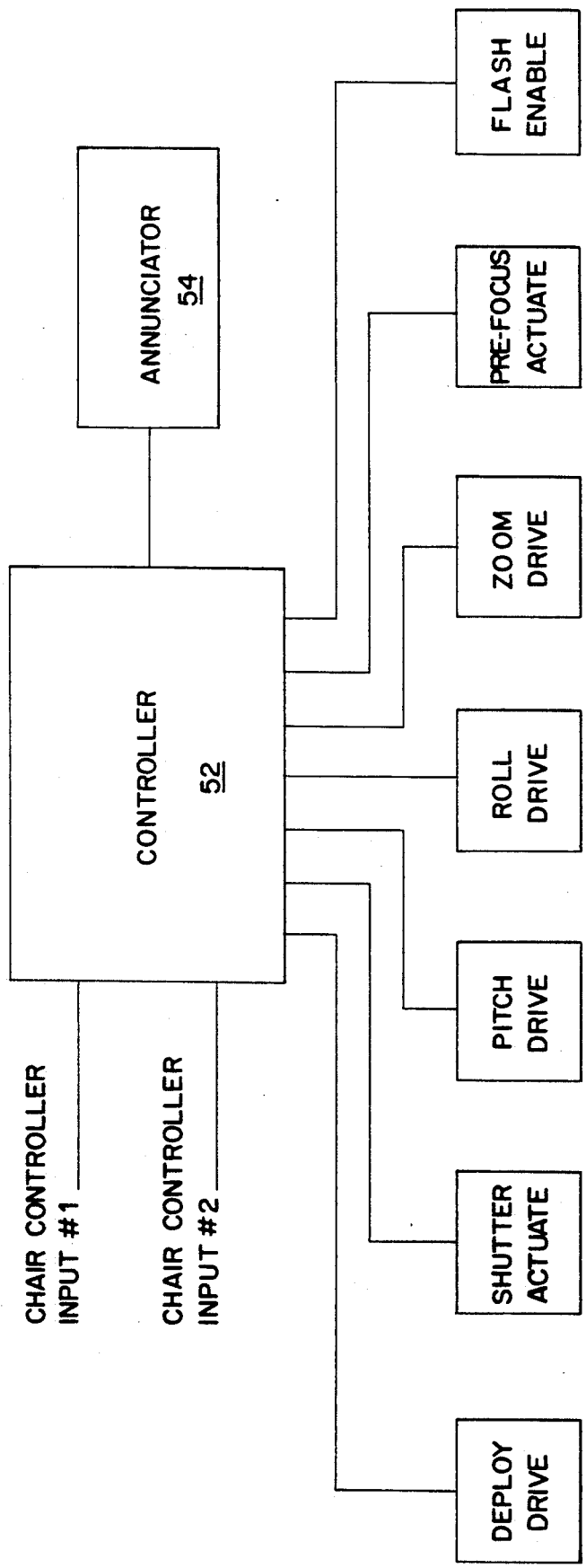
FIG. 11 is a block diagram of the control system of the apparatus.

Referring now to FIG. 11, the operation of the controller 52 for controlling the operation of the various functions of the apparatus 10 is schematically illustrated. The controller 52 is responsive to the two output relays of the chair controller for operating in seven different modes in order to control seven different functions as listed below.
1) Deploy drive
2) Shutter actuate
3) Pitch Drive
4) Roll drive
5) Zoom drive
6) Prefocus actuate
7) Flash enable The controller 52 as herein embodied comprises a conventional logic circuit including a plurality of AND gates, OR gates, FLIP-FLOPS, Relays, and switch debouncers which are interconnected in a conventional manner to enable the controller 52 to selectively control the various functions of the apparatus 10. It will be understood, however, that the functions of the controller 52 could alternatively be implemented with a conventional microprocessor which is programmed through conventional techniques for performing the functions described. The controller 52 is preferably connected to the chair controller (not shown) so that by sipping on the control member 36 a signal is sent to the controller 52 through the chair controller Input No. 1, and so that by puffing on the control member 36 a signal is sent to the controller 52 through the chair controller Input No. 2. The controller is further preferably adapted so that each sip on the control member 36 causes the controller 52 to shift to a different mode in a predetermined sequence and so that each puff on the control element 36 causes the controller 52 to operate within the designated mode to either carry out an actuation or an adjustment of the corresponding chair function. The annunciator 54 is preferably attached to the wheelchair annunciator 37 so that it can be readily observed by the operator 16 for determining the mode in which the controller 52 is operating at any given time.

Considering first the deploy drive mode of the controller 52, this mode is operative for deploying the apparatus 10 to an operative position by raising the second arm portion 44 to position the camera 14 so that the viewfinder 38 thereof is substantially aligned with the right eye of the operator 16. More specifically, the deploy drive function of the controller 52 is operative for controlling the operation of the motor 70 to move the second arm assembly 44 between the inoperative position thereof and the operative position thereof. In this connection, once the controller has been actuated to raise the second arm assembly 44 to the operative position thereof as defined by the microswitch 122, a second puff causes the motor 70 to move the second arm assembly 44 to the inoperative position thereof as defined by the microswitch 124.

The shutter actuate mode of the controller 52 is connected to the remote shutter control input of the camera 114 and it is operative for triggering the shutter of the camera 14. Specifically, the shutter of the camera 14 can be actuated by sipping on the control member 36 with a series of relatively short sips until the controller 52 is switched to the shutter mode and then puffing on the control member 36 to actuate or trigger the shutter.

The pitch drive mode of the controller 52 is operative for controlling the operation of the second arm portion 44 to control the tilt angle or pitch of the camera 14 as it is pivoted about the tilt axis 160. More specifically, the pitch drive mode is operative for actuating the motor 138 to adjust the pitch of the camera 14 by adjusting the position of the tilt arm 46 relative to the second arm portion 44. Once the controller 52 is in the pitch drive mode, the pitch drive function is operative by puffing on the control member 36 to actuate the motor 138 in a first direction, puffing a second time to stop the motor 138, and puffing a third time to actuate the motor 138 in a reverse direction. The pitch drive function is also responsive to the micro switches 156 for reversing the direction of the motor 138 when the drive member 154 reaches a limit position on the shaft 146.

The roll drive mode of the controller 52 is operative for controlling the travel of the carriage assembly 50 on the track member 72. When the controller is in the roll drive mode and the operator 16 emits a puff to the control member 36, the controller is operative of actuating the motor 198. Specifically, a first puff on the control member 36 causes the motor 198 to be actuated in a first direction, the second puff causes the motor 198 to be stopped, and a third puff causes the motor 198 to be actuated in a reverse direction. The roll drive mode of the controller 52 is also responsive to the micro switch 215 for reversing the direction of the motor 198 when the carriage assembly 50 reaches the limit of its travel in either direction.

The zoom drive function of the controller 52 is operative in a manner similar to the roll drive. When the controller 52 is in the zoom drive mode the control member 36 can be operated for controlling the operation of the motor 217 to control the zoom function of the camera 14. Specifically, a first puff on the control member 36 causes the motor 217 to be actuated in a first direction, a second puff causes the motor 217 to be stopped, and a third puff causes the motor 217 to be actuated in a reverse direction. The zoom drive function is also responsive to the micro switch 234 for reversing the direction of the motor 217 when the zoom lens 40 reaches either the maximum or the minimum zoom position.

The prefocus actuate mode of the controller 52 is operative for controlling the solenoid 240 in order to actuate the auto focus function of the camera 14 by partially depressing the shutter button thereof. The prefocus mode is responsive to one of the mercury switches 162 for deactuating the prefocus function when the camera 14 and the second arm portion 44 are in inoperative positions. When the controller 52 is in the prefocus mode, the controller 52 is operative for controlling the solenoid 240 to actuate the prefocus function with a single puff on the control member 36 and it is operative for deactuating the prefocus function with a second puff. Further, the prefocus function is deactuated after the shutter has been triggered.

The flash mode of the controller 52 is operative for enabling or disabling the flash attachment 40a which is mounted on the carriage assembly 50 so that when the flash attachment 40a is enabled it is actuated with the shutter of the camera 14. The flash attachment 40a is enabled by shifting the controller 52 to the flash enable mode by sipping on the control member 36. Once the controller 52 is in the flash enable mode the flash attachment 58 can be enabled by puffing on the control member 36 and it can be disabled by puffing a second time on the control member 36.

Accordingly, for use and operation of the apparatus 10 in combination with the camera 14, the apparatus 10 is initially adjusted by a person assisting the operator 16 so that the camera 14 is loaded with film and properly positioned in front of the face of the operator 16 when the camera 14 is moved to an operative position with apparatus 10. Specifically, the angle of the first arm portion 42 is adjusted with the adjustment knob 98 to adjust the elevational position of the camera 14 when the apparatus 10 is in the operative position thereof, and the positions of the micro switches 122 and 124 on the threaded rods 114 and 116 are adjusted by manipulating the associated adjustment knobs. Specifically, the micro switches 122 and 124 are adjusted to set the distance between the camera 14 and the eye of the operator 16 when the apparatus 10 is in the operative position and the distance between the camera 14 and the lap of the operator 16 when the apparatus 10 is in the inoperative position, respectively. The tension on the chain 110 is also adjusted utilizing the adjustment screw 130, and the lateral position of the camera 14 is adjusted relative to the eye of the operator 16 with the nut 136. Thereafter, the operator 16 can operate the camera utilizing the apparatus 10 to take photographs as desired. In this regard, the tilt angle of the camera 14 can be adjusted utilizing the pitch drive of the controller 52 to pivot the tilt arm portion 46 about the axis 160. The camera 14 can be moved from side to side by operating the wheelchair 12 to move from side to side in a conventional manner, and the camera 14 can be rotated about the viewfinder axis 39 in order to properly frame a photographic subject in the viewfinder 38. Once the photographic subject has been properly located in the viewfinder 38, the zoom drive can be operated to adjust the magnification of the photographic subject in the viewfinder 38, and once the subject has been properly located in the viewfinder 38, the prefocus function can be actuated to operate the automatic focus function of the camera 14. Depending on whether or not the flash attachment 40a is required, the controller 52 can be shifted to the flash enable mode to either enable or disable the flash attachment 40a. Finally, once the camera has been properly positioned and set, the controller can be operated in the shutter mode to enable the operator 16 to take one or more photographs at will.

It is seen therefore that the instant invention provides an effective apparatus for enabling a severely handicapped person to take photographs. The apparatus 10 can be effectively manipulated by the operator 16 utilizing the control member 36 to adjust the camera 14 and to properly position it relative to a photographic subject so that the operator 16 can take high-quality photographs despite his or her physical disability. Accordingly, it is seen that the instant invention represents a significant advancement in the art relating to apparatus for severely handicapped persons and that it therefore has both humanitarian and commercial significance.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A robotic photographic apparatus for use by a handicapped operator having an upper body disability to enable said operator to robotically operate a camera while seated in a chair, said camera having a view finder, said apparatus comprising manipulating means for robotically holding and manipulating said camera, mounting means for mounting said manipulating means on said chair, and control means operable by said person for controlling the operation of said manipulating means while seated in said chair, said manipulating means being operable through said control means for moving said camera between an operative position wherein said camera is positioned in front of the face of said operator and an inoperative position wherein said camera is removed from in front of the face of said operator.

2. In the apparatus of claim 1, said manipulating means including first and second arm portions, said mounting means mounting said first arm portion in substantially stationary relation to said chair, said second arm portion being pivotable relative to said first arm portion for raising and lowering said camera between said inoperative and operative positions thereof.

3. In the apparatus of claim 1, said viewfinder having a viewing axis, said manipulating means including means for rotating said camera substantially about said viewing axis.

4. In the apparatus of claim 2, said mounting means adjustably mounting said first arm portion so that said first arm portion is adjustably positionable relative to said chair but so that said first arm portion is normally substantially stationary during operation of said manipulating means with said control means.

5. In the apparatus of claim 1, said viewfinder having a viewing axis, said manipulating means including tilt means for tilting said camera to tilt said viewing axis upwardly and downwardly.

6. In the apparatus of claim 5, said tilt means tilting said camera about a point on said viewing axis which is between approximately ⅞" and 3" from said viewfinder.

7. In the apparatus of claim 1, said camera having an adjustable zoom lens, said manipulating means including means for adjusting said zoom lens.

8. In the apparatus of claim 1, said camera having an adjustable focus, said manipulating means including means for adjusting the focus of said camera.

9. In the apparatus of claim 1, said camera including a flash, said manipulating means including means for manipulating said camera to enable said flash.

10. In the apparatus of claim 2, said viewfinder having a viewing axis, said manipulating means including an arcuate track member on said second arm portion, and a carriage member traveling on said track member, said camera being mounted on said carriage member and being movable on said track member for rotating said camera about said viewing axis.

11. A robotic photographic apparatus for use by a handicapped operator having an upper body disability to enable said operator to robotically operate a camera while seated in a chair so that the head of said operator is in a predetermined substantially stationary orientation, said operator having an eyeball and a nose, said camera having a viewfinder, said apparatus comprising manipulating means for robotically holding and manipulating said camera, mounting means for mounting said manipulating means on said chair, and control means operable by said operator for controlling the operation of said manipulating means while seated in said chair for moving said camera between an operative position wherein said camera is positioned in front of the face of said operator so that said viewfinder is substantially aligned with said eyeball and an inoperative position wherein said camera is removed from in front of the face of said operator.

12. In the apparatus of claim 11, said viewfinder having a viewing axis, said manipulating means including means for rotating said camera about said viewing axis.

13. In the apparatus of claim 12, said manipulating means including tilt means for tilting said camera to tilt said viewing axis upwardly and downwardly about a point along said viewing axis which is between approximately ⅞" and 3" from said viewfinder.

14. In the apparatus of claim 11, said viewfinder having a viewing axis, said manipulating means including tilt means for tilting said camera to tilt said viewing axis upwardly and downwardly about a predetermined pivot point, said manipulating means being adjustable for positioning said pivot point at approximately the geometric center of said eyeball.

15. In the apparatus of claim 11, said operator facing in a predetermined direction when in said predetermined position, said manipulating means positioning said camera at an angle of approximately 20° to said predetermined direction in a direction tilting said camera away from the nose of said operator when said camera is in said operative position.

* * * * *